US006343860B1

(12) United States Patent
Pierotti

(10) Patent No.: US 6,343,860 B1
(45) Date of Patent: Feb. 5, 2002

(54) TORIC-SHAPED LENSES AND GOGGLE ASSEMBLY

(75) Inventor: Elizabeth M. Pierotti, Little Compton, RI (US)

(73) Assignee: Greenhouse Grown Products, Inc., Little Compton, RI (US)

( * ) Notice: Subject to any disclaimer, the term of this patent is extended or adjusted under 35 U.S.C. 154(b) by 0 days.

(21) Appl. No.: 09/645,339

(22) Filed: Aug. 25, 2000

Related U.S. Application Data

(60) Provisional application No. 60/150,803, filed on Aug. 26, 1999.

(51) Int. Cl.$^7$ .............................. G02C 7/02; G02C 7/10
(52) U.S. Cl. .......................... 351/159; 351/44; 351/157
(58) Field of Search ......................... 381/159, 41, 158, 381/177, 178, 43, 44, 176, 157

(56) References Cited

U.S. PATENT DOCUMENTS

| | | |
|---|---|---|
| 2,088,262 A | 7/1937 | Grano |
| 3,040,616 A | 6/1962 | Simpson |
| 3,672,750 A | 6/1972 | Hagen |
| 4,447,914 A | 5/1984 | Jannard |
| D311,197 S | 10/1990 | Jannard |
| D320,402 S | 10/1991 | Jannard et al. |
| D323,333 S | 1/1992 | Jannard et al. |
| D324,394 S | 3/1992 | Jannard |
| D324,528 S | 3/1992 | Jannard |
| D325,040 S | 3/1992 | Jannard |
| 5,093,940 A | 3/1992 | Nishiyama |
| 5,094,520 A | 3/1992 | Reshef et al. |
| D328,468 S | 8/1992 | Jannard |
| D329,445 S | 9/1992 | Jannard |
| D330,035 S | 10/1992 | Jannard |
| D330,716 S | 11/1992 | Jannard |
| D330,903 S | 11/1992 | Jannard |
| D331,587 S | 12/1992 | Jannard et al. |
| D331,763 S | 12/1992 | Jannard |
| D333,145 S | 2/1993 | Jannard |
| D335,887 S | 5/1993 | Jannard |
| D336,908 S | 6/1993 | Jannard |
| 5,249,001 A | 9/1993 | Jannard |
| D342,534 S | 12/1993 | Jannard et al. |

(List continued on next page.)

OTHER PUBLICATIONS

"Whatever your passion . . . " Flyer—©2000/2001 by GreenHouse Grown Products, Inc.
J.K. Crosley et al., U.S. Army Aeromedical Research Laboratory (USAARL) Report No. 91–13 (03/91), cover and pp. 4–5.
R. M. Wildzunas, U.S. Army Aeromedical Research Laboratory (USAARL) Report No. 96–07 (01/96), cover and p. 1137.
R. R. Levine et al., U.S. Army Aeromedical Research Laboratory (USAARL) Report No. 90–12 (05/90), cover and p. 5.
Material at http://www.ilcdover.com/products/CB-SysMasks/M43.htm and two photographs.
N. R. Brletich et al., Worldwide NBC Mask Handbook (Defense Technical Information Center, Alexandria, Va. (09/92)), pp. 389–393.

*Primary Examiner*—Hung Xuan Dang
(74) *Attorney, Agent, or Firm*—Westerlund-Powell, P.C.; R. H. J. Powell; Robert Westerlund

(57) ABSTRACT

The present invention relates to toric-shaped see through lenses used in eyewear. The lenses have a substantially constant thickness and having base curve with a substantially constant radius of curvature of at least 15 mm and preferably in the range of 19–23 mm. The toric lenses may be supported in a frame formed of either rigid or flexible material and attached to a strap assembly adaptable to be worn by the user. Optionally, each of the lenses may be supported by a flanged member and ventilation passages preferably extending through the frame and/or the lenses to allow air to circulate around the lenses.

23 Claims, 8 Drawing Sheets

U.S. PATENT DOCUMENTS

| | | |
|---|---|---|
| D342,959 S | 1/1994 | Jannard et al. |
| D343,182 S | 1/1994 | Jannard |
| D344,281 S | 2/1994 | Jannard et al. |
| D344,742 S | 3/1994 | Jannard |
| 5,313,671 A | 5/1994 | Flory |
| 5,359,371 A | 10/1994 | Nolan |
| D354,968 S | 1/1995 | Jannard |
| 5,387,949 A | 2/1995 | Tackles |
| D356,323 S | 3/1995 | Yee |
| D356,324 S | 3/1995 | Yee |
| D358,600 S | 5/1995 | Jannard |
| D358,829 S | 5/1995 | Jannard et al. |
| D359,302 S | 6/1995 | Yee et al. |
| D359,748 S | 6/1995 | Yee |
| D359,749 S | 6/1995 | Yee |
| D359,971 S | 7/1995 | Jannard |
| D365,357 S | 12/1995 | Jannard et al. |
| D365,591 S | 12/1995 | Jannard et al. |
| D368,921 S | 4/1996 | Yee et al. |
| D369,375 S | 4/1996 | Jannard et al. |
| 5,541,674 A | 7/1996 | Jannard |
| 5,550,599 A | 8/1996 | Jannard |
| D374,448 S | 10/1996 | Yee et al. |
| D376,162 S | 12/1996 | Yee et al. |
| D376,163 S | 12/1996 | Jannard et al. |
| D376,609 S | 12/1996 | Yee et al. |
| D377,498 S | 1/1997 | Jannard et al. |
| 5,604,547 A * | 2/1997 | Davis et al. ................ 351/44 |
| 5,610,668 A | 3/1997 | Mage |
| 5,625,425 A | 4/1997 | Kranhouse |
| 5,638,145 A | 6/1997 | Jannard et al. |
| 5,648,832 A | 7/1997 | Houston et al. |
| D384,362 S | 9/1997 | Yee |
| D384,364 S | 9/1997 | Yee |
| D384,686 S | 10/1997 | Jannard et al. |
| D385,291 S | 10/1997 | Jannard et al. |
| 5,689,323 A | 11/1997 | Houston et al. |
| D388,816 S | 1/1998 | Jannard et al. |
| 5,708,489 A | 1/1998 | Jannard |
| D392,662 S | 3/1998 | Jannard et al. |
| 5,730,155 A | 3/1998 | Allen |
| 5,732,415 A | 3/1998 | Boyd |
| 5,760,868 A | 6/1998 | Jannard et al. |
| 5,774,201 A | 6/1998 | Tackles |
| D397,132 S | 8/1998 | Yee |
| D397,350 S | 8/1998 | Jannard et al. |
| D398,022 S | 9/1998 | Jannard et al. |
| D398,326 S | 9/1998 | Jannard et al. |
| 5,801,805 A | 9/1998 | Mage |
| 5,805,261 A | 9/1998 | Houston et al. |
| D399,239 S | 10/1998 | Jannard et al. |
| D399,240 S | 10/1998 | Jannard et al. |
| D399,243 S | 10/1998 | Jannard et al. |
| D399,519 S | 10/1998 | Yee |
| D399,865 S | 10/1998 | Jannard et al. |
| D399,866 S | 10/1998 | Yee |
| D402,304 S | 12/1998 | Jannard et al. |
| D404,747 S | 1/1999 | Yee et al. |
| D404,754 S | 1/1999 | Yee et al. |
| D405,102 S | 2/1999 | Moritz et al. |
| D407,428 S | 3/1999 | Jannard et al. |
| D408,049 S | 4/1999 | Jannard et al. |
| D410,484 S | 6/1999 | Jannard et al. |
| D410,485 S | 6/1999 | Jannard et al. |
| 5,915,542 A | 6/1999 | Swiet |
| 6,142,624 A | 11/2000 | Morris et al. ................ 351/159 |

* cited by examiner

TORIC-SHAPED LENSES AND GOGGLE ASSEMBLY

PROVISIONAL APPLICATION

The present applicant respectfully requests priority based on Provisional Application No. 60/150,803, which was filed Aug. 26, 1999 in the name of inventor Elizabeth M. Pierotti, a named inventor of the present invention. The Provisional Patent Application is incorporated herein by reference for all purposes.

BACKGROUND OF THE INVENTION

1. Field of the Invention

The present invention relates to see-through lenses. More particularly, the present invention is directed to uniquely constructed, toric-shaped lenses adaptable primarily for use in non-prescription sunglasses, sport goggles and the like.

2. Description of the Related Art

As well as enhancing vision, eyeglasses also serve to protect the eye against all types of foreign objects. Initially, the lenses employed in such eyeglasses were routinely made of glass and were substantially flat in shape, a condition which created significant distortion around the periphery of the lenses. More recently, lenses have been made of a variety of plastic or plastic-like materials, often having dramatically curved surfaces. For example, swim or riding goggles are well know to have teardrop-shaped lenses. While such lenses may reduce aerodynamic drag, a wearer may suffer from undesirable peripheral distortion when viewing through such lenses.

Curved lenses employed in sports goggles, sun glasses or the like may be more or less elliptical in shape as required by the specific application. Such applications may include fashion eye wear, performance eye wear including swim and sport goggles, and sunglasses, as well as all manner of protective eye wear for use at home and on the job. In any particular use, the arc of the curved lens may vary in shape dependent on the overall circumference of the curved lens necessary to achieve undistorted vision. Lenses may be employed with a slight spherical appearance, i.e., a modified toric or ovoid arc. In such slightly curved lenses, there is a variable radius of curvature somewhere between 8–12 mm, e.g., a 12 base curve. In effect, the distance between the lens and eye may well differ at different locations on the lens. This may create significant distortion at the periphery of each lens.

The Government of the United States has procured a protective facemask assembly having a pair of semi-curved lenses of toric or ovoid configuration. While these lenses may seem superficially similar to the present invention, closer inspection reveals a number of significant differences. Because the Government lenses are mounted in pockets creating the nose bridge of the facemask, the edge of each Government lens is truncated or cut-off to allow for assembly into its respective pocket. This naturally creates peripheral distortion for the wearer of the mask, when attempting to view through the truncated portion located near the mask nose. Another drawback of the Government procured toric lens is the use of only a single size lens, i.e.; "one size fits all." Each Government lens also incorporates two parts, a toric lens and surrounding flange joined by a dedicated and detectable seam. This seam itself can distort the vision of the wearer. Furthermore, there is no suggestion that the flange surrounding the Government's toric lens can be made of any desirable configuration.

It is clear that there exists a need in the art for an improved viewing lens capable of providing distortion free viewing in a fashionable design equally adaptable for use in most all types of eyewear including conventional, non prescription sunglasses. As will become apparent, the present invention provides a uniquely configured bugeyes® lens assembly which optimizes peripheral vision while minimizing the size of each lens and thus maximizing the aerodynamic flow of air around the lens.

SUMMARY OF THE INVENTION

There is a need in the art for eyewear lenses capable of providing maximum field-of-view with a minimum of distortion. Such lenses need be adaptable for eyewear including sports wear and fashion wear. The present invention provides such unique toric-shaped lenses and associated eyewear.

The present invention is directed to a unique, toric-shaped lens adaptable for use as a viewing lens in protective eyewear, sunglasses, sport goggles and swim wear utilized above the water. The invention includes a unique Bugeyes® lens wherein the radius of curvature of the lens is substantially constant from a normal eyeball as it scans throughout the viewing field. Because the radius of curvature is substantially constant, the toric-shaped, Bugeyes® lens provides for continuous, undistorted peripheral vision. The radius of curvature of the lens is greater than 15 mm and preferably in the range of 19–23 mm, e.g., an exemplary lens with a base curve in the range of 19–23.

The Bugeyes® lens is of substantially constant thickness throughout the field of view and the lens is optically correct and free from any prism effect throughout the periphery of the lens. The lens has a 0 power of magnification at all points in the viewing field when constructed of material having an index of refraction of between 1.57 and 1.60. A further feature of the present invention is that the closer the lens is positioned relative to the eye, the smaller in size the lens needs be. The lens should be no smaller than necessary to provide freedom of movement of the wearer's eyelashes. As the separation between the lens and the eye increases, the size of the lens will also increase, with the maximum practical size of the lens directly related to the facial geometry and to the point at which the wearer's eyes field of vision overlap.

A pair of toric-shaped lenses according to the present invention may be directly attached to a pair of stems (also referred to as temples) extending about opposite sides of the wearer's head or attached to a goggle strap of any size and shape. Each toric-shaped lens may include a flange portion partially or totally surrounding the viewing lens. At the point where the lens and flange intersect, a seam may exist which visually differentiates between the lens and the flange. In one embodiment of the present invention, the lens and surrounding flange are separately constructed and joined at the seam. Alternatively, the lens and flange may be integrally constructed out of the same material with a gradual transition between the lens and flange portions providing a seamless appearance. Regardless of the type of construction employed, these flanges may serve to secure the lenses to a pair of eyeglass stems, padding, nose piece, ear piece, strap or the flange may be purely ornamental. The flange can be of any size, shape, color, texture or material. It is also within the scope of the present invention to dispense with the flange altogether by directly connecting each toric-shaped lens to the goggle or glass frame.

The percentage of the toric lens which must be used for the field-of-view should be sufficient to provide undistorted peripheral vision of at least 20° vertical and 20° horizontal and may be as great as 80° to 94° at the distal portion of each lens. As the proximal portion of the toric lens, the nose would restrict overall monocular vision to field-of-view of about 140° to 156°.

BRIEF DESCRIPTION OF THE DRAWINGS

The various advantages of the present invention will become apparent to one skilled in the art by reading the following specification and by reference to the following drawings in which.

DESCRIPTION OF THE INVENTION

Figure 1:
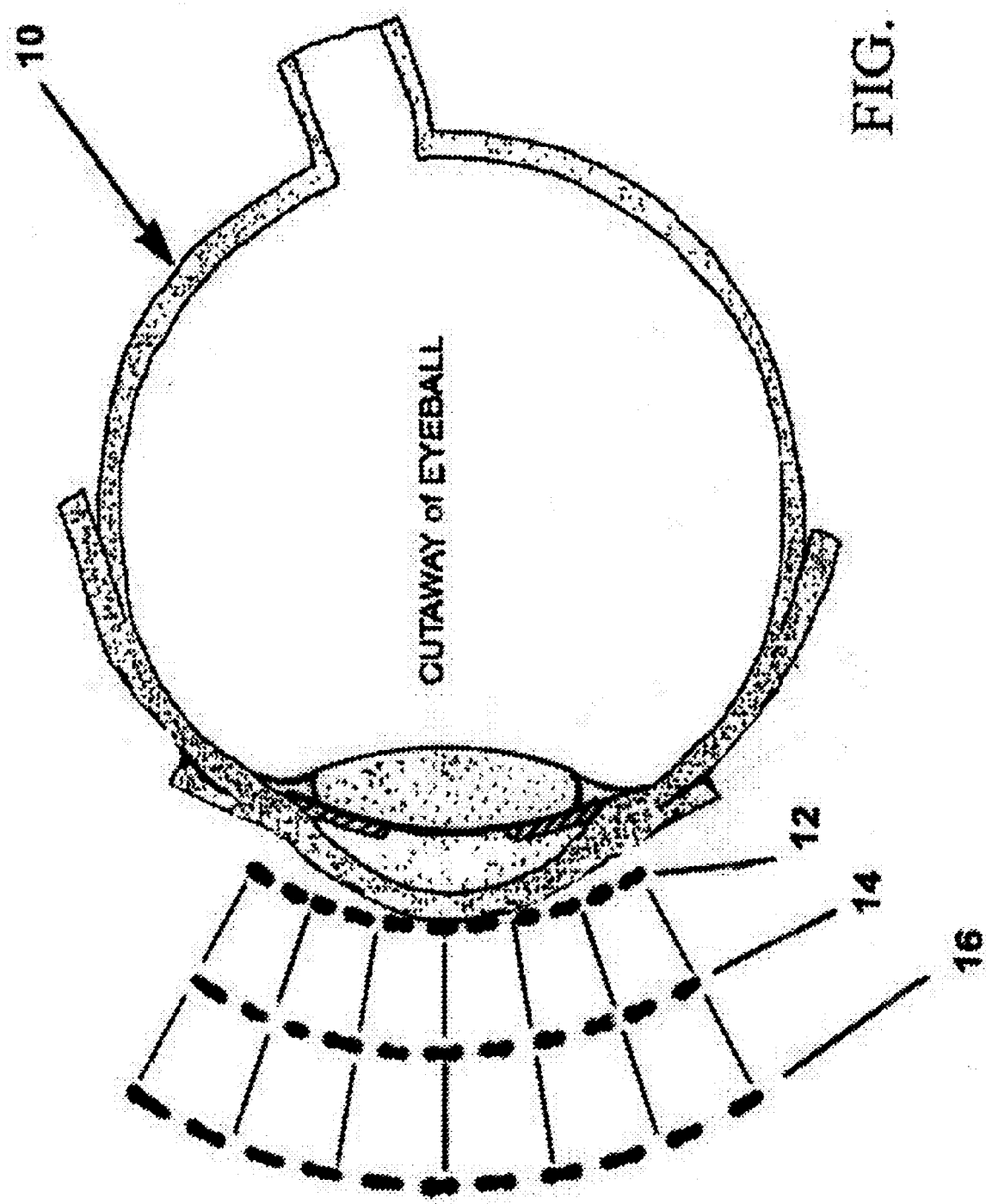
FIG. 1 is a cross-sectional view of an eyeball and two curved lenses formed in accordance with the present invention.

Illustrative embodiments and exemplary applications are described below with reference to the accompanying drawings in order to disclose the advantageous teachings of the present invention. Referring now to the drawings wherein like reference numerals designate like elements throughout, a typical eyeball is shown in cross-section in FIG. 1 at 10. The dotted line 12 traces the shape of the eyeball as it scans the field-of-view. The dotted lines 14 and 16 each show the shape of a toric lens formed in accordance with the present invention. The toric lens 14 is at all times substantially equal distance from the line 12 delineating the eyeball 10. In a similar manner, the toric lens 16 is also at all times substantially equal distance from the line 12 of the eyeball 10. As will be understood, the lens 14 has a smaller radius of curvature than the lens 16. The difference in size between the lenses 14 and 16 results in a different field-of-view when scanned by eyeball 10. Whether a toric lens the size and shape of lens 14 or the size and shape of lens 16 is employed would depend on the desired field-of-view.

Figure 2A:
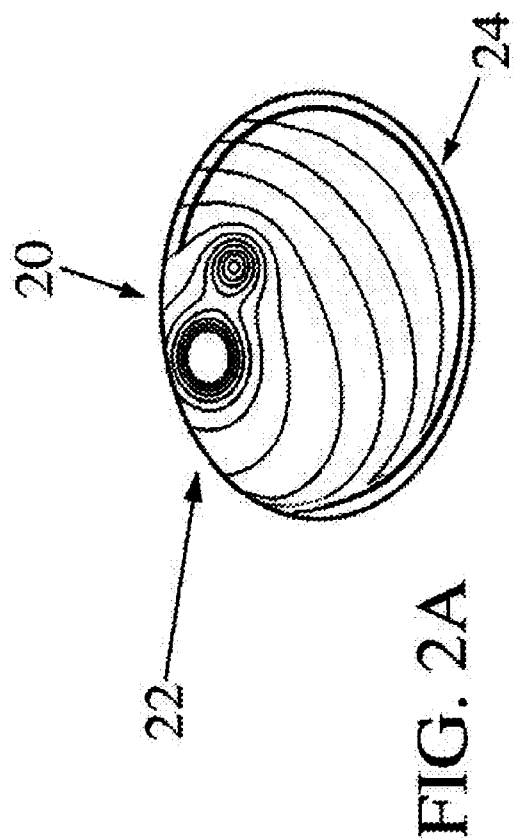
FIGS. 2a, 2b, 2c and 2d are face, side, top and back views, respectively, of a toric-shaped lens formed in accordance with the present invention.
Figure 2B:
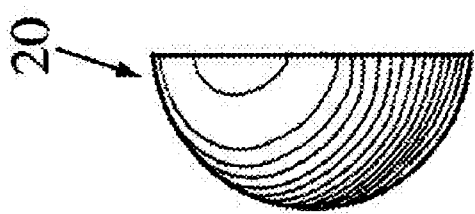
Figure 2C:
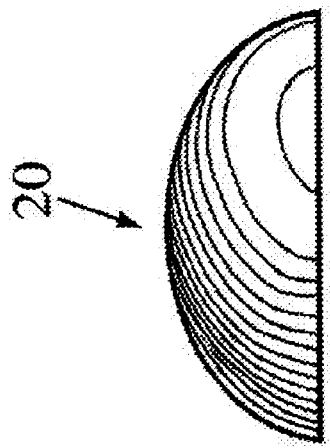
Figure 2D:
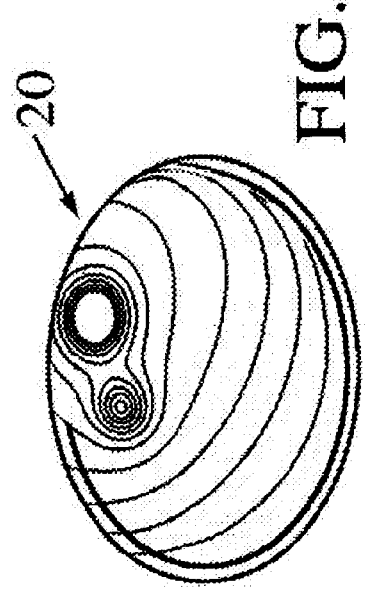

Turning now to FIGS. 2a, 2b, 2c, 2d, wherein various views are shown of a toric-shaped lens 20 formed in accordance with the present invention. Lens 20 has a substantially constant radius of curvature, i.e., base curve, of at least 15 mm and preferably in the range of 19–23 mm, at least along the toric axis. As also shown in FIG. 2a, the toric shape of lens 20 is similar to the shape of half an eggshell. The thickness of toric lens 20 is constructed to be substantially constant throughout. The percentage of the toric shape of lens 20 used for viewing sufficient to provide undistorted peripheral vision of 20° vertical and 20° horizontal is between 80° and 94° at the distal portion 22 of the lens and between 140° and 156° at the proximal portion 24 of the lens.

Figure 3B:
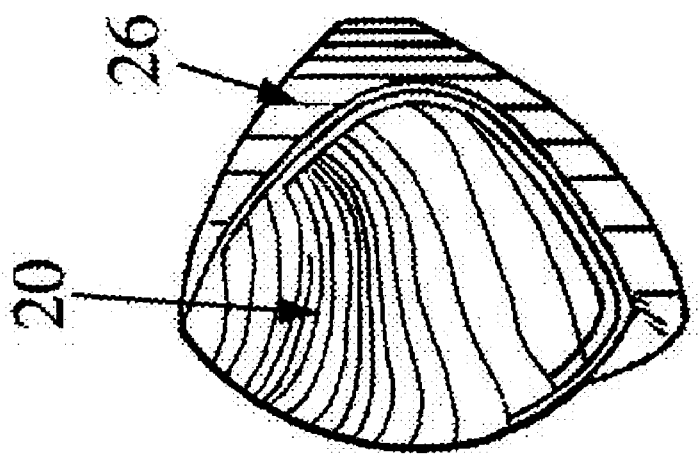
FIGS. 3a and 3b are front and side views, respectively, of a toric lens mounted in a flange and formed in accordance with the present invention.
Figure 3A:
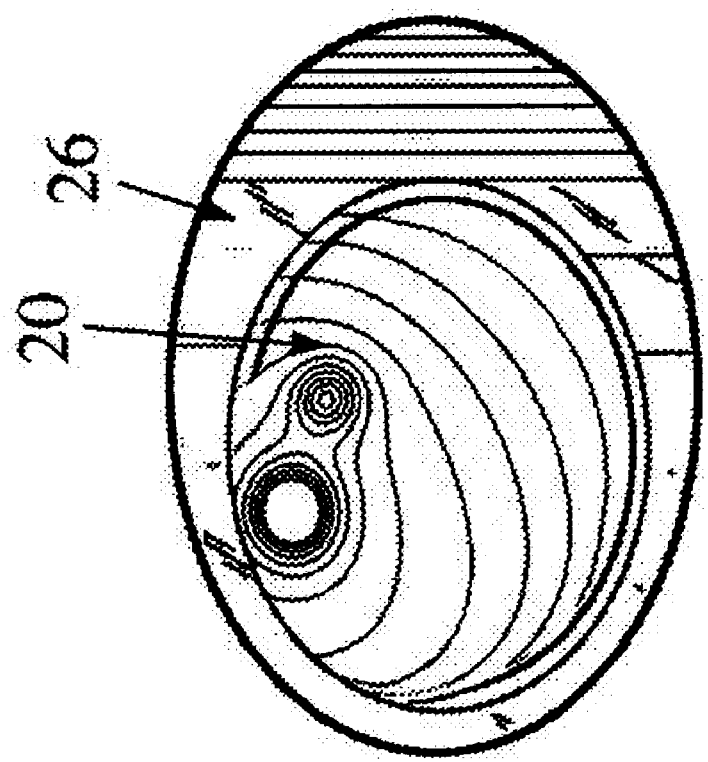

Turning to FIGS. 3a and 3b, toric lens 20 includes a surrounding flange portion 26. Flange 26 joins and supports toric lens 20 while providing points of attachment for connecting lens 20 to the frame portion of glass wear or goggles. Flange 26 may be formed of any convenient shape. As shown in FIG. 3b, flange 26 includes an elongated portion 28 located near the distal end of lens 20 remotely positioned from the adjacent lens as discussed below.

Figure 4:
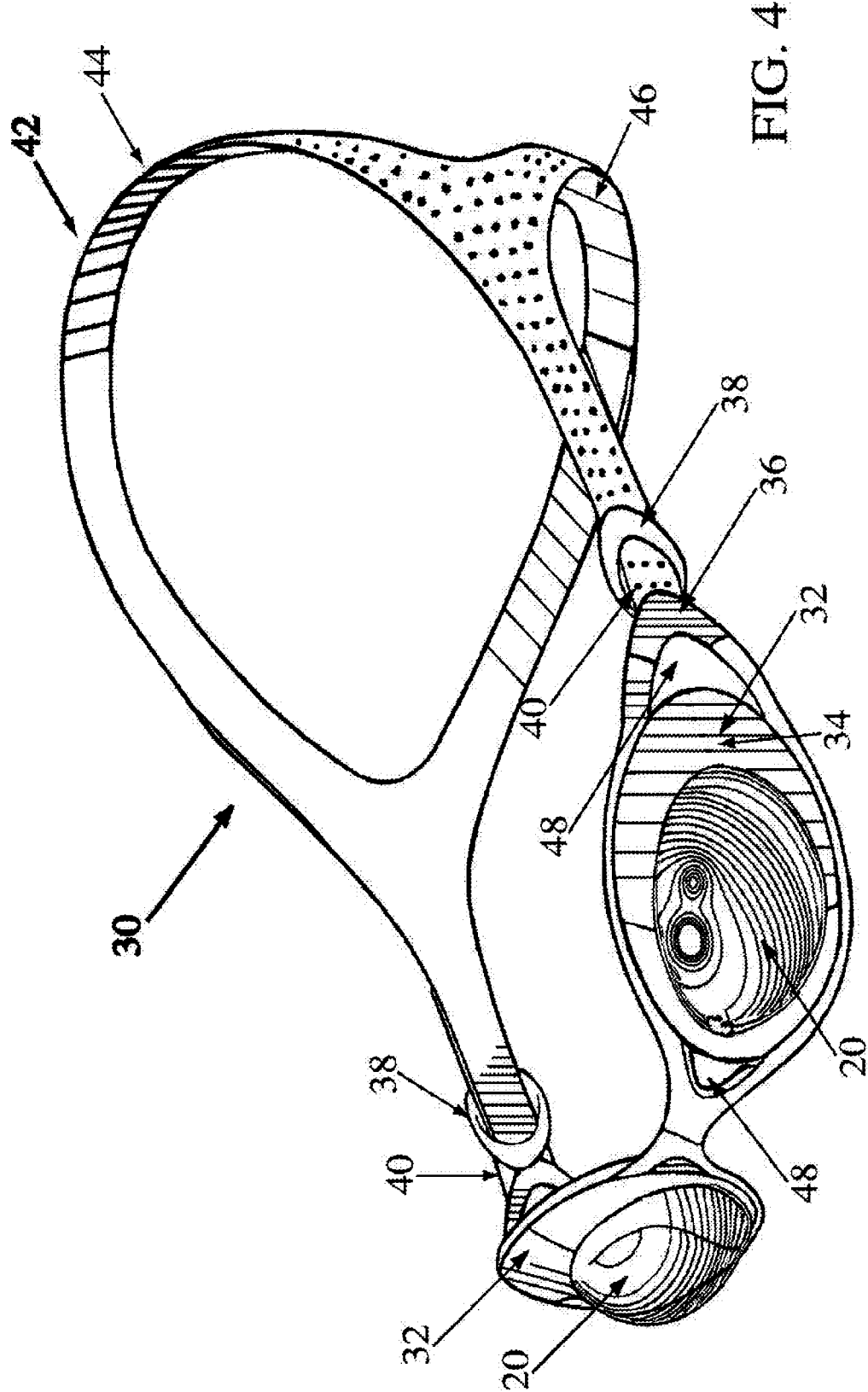
FIG. 4 is a perspective view of a performance goggle assembly formed in accordance with the present invention and including a pair of toric-shaped lenses formed in accordance with the embodiment of FIGS. 3a and 3b of the present invention.

Referring now to FIG. 4, a radical performance sport goggle assembly is generally indicated at 30. Goggles 30 include a pair of toric-shaped lenses 20 each formed in accordance with the present invention. Each of the lenses 20 has a substantially constant radius of curvature of at least 15 mm and preferably in the range of 19–23 mm. Each of the lenses 20 is mounted in a frame or holder 30. Holder 30 may be formed of a hard plastic material or, preferably, may be formed of soft, impact resistant material. Holder 30 includes a pair of elongated eye piece openings 34, with each opening 34 releasably retaining in place one lens 20. A particular retention assembly may comprise conventional clips, snaps or other fasteners mounted on holder 30. When desired, each of the lenses 20 may be detached and replaced by different size lenses of the same or a different color. Holder 32 further includes end portions 36 with quick-release loop connector members 38 preferably formed of stretchable rubber, which may selectively enclose and retain opposite ends 40 of a strap 42 designed to extend around the wearer's head. By pulling the connector members 38 away from the wearer's face, it is possible to tighten the frame 30 and strap 42 about the wearer's head without forming any dangling ends. The strap 42 is preferably formed of sweat-absorbing material and may comprise a single band or two separate and yet connected band portions 44 and 46 which provide an ergonomic opening for secure and comfortable fit. As also shown in FIG. 4, a number of air flow/ventilation openings 48 are created between walls of each opening 34 and the toric lenses 20. Because a considerable amount of air is allowed to move behind each of the lenses 20, they will not fog up as readily as conventional eyewear.

A particular benefit of the toric lens 20 is its ability to be worn closer to the face than conventional eyewear. This is due to the radical radius of the Bugeyes® lens 20. Even though the lens 20 closely fits over the wearer's eye, the eyelashes will have sufficient room to open and close without interference from the inside wall of the lens 20. Because the lens 20 is much closer to the eye then with conventional eyewear, there is a significant improvement of the peripheral vision. Such improved peripheral vision may provide the wearer with superior advance warning of potential danger at the periphery of the lens. Likewise, when a foreign object impacts the face, the fact that lens 20 is closer to the face because of its unique toric configuration, means that the distance that the impacted lens 20 moves is reduced, cushioning the blow to the face.

Figure 5:
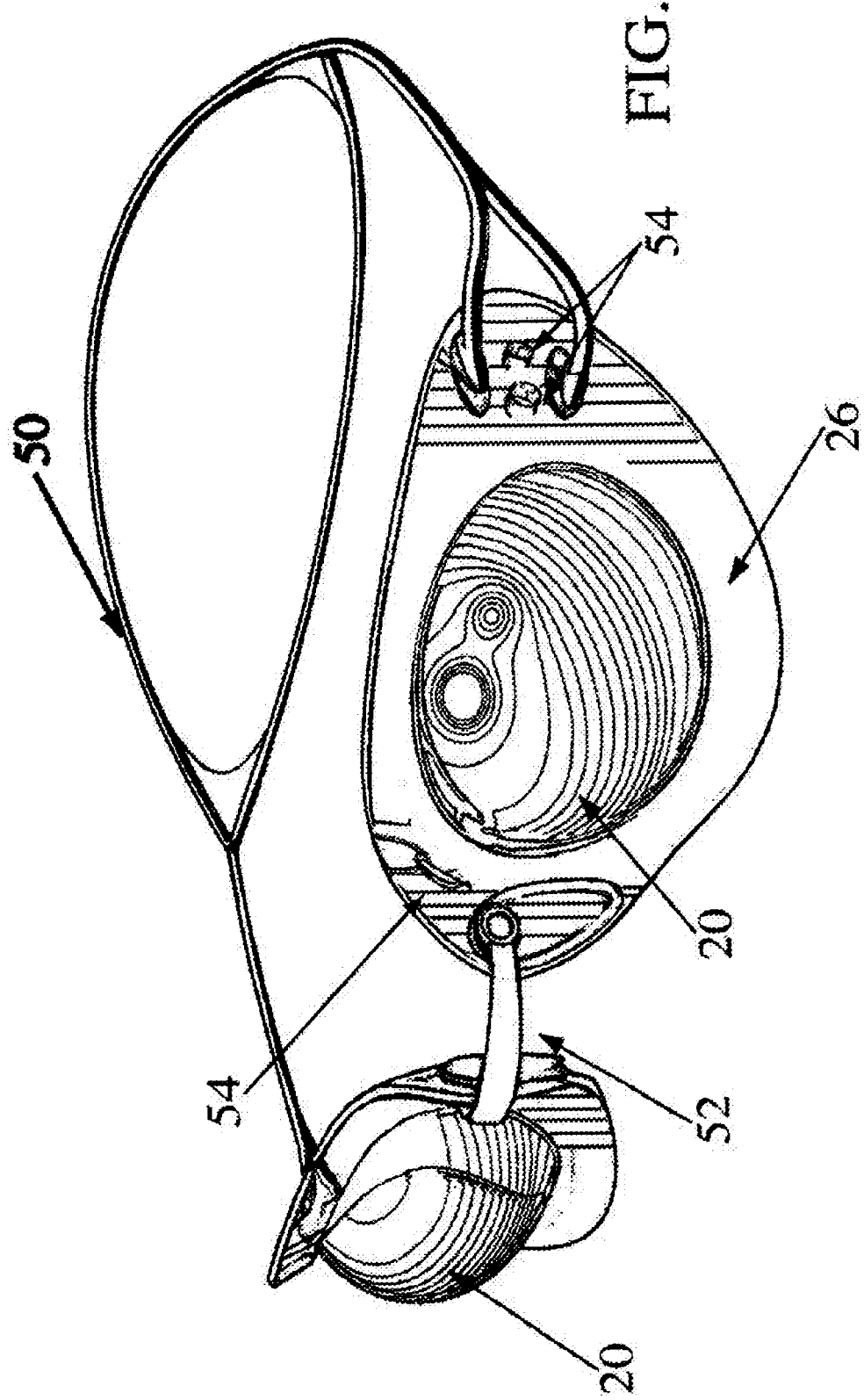
FIG. 5 is a perspective view of a further performance goggle assembly formed in accordance with the present invention and including a pair of toric-shaped lenses formed in accordance with the embodiment of FIGS. 3a and 3b of the present invention.

Instead of employing a frame or holder 34, the toric-shaped lenses 20 and surrounding flanges portions 26 may be directly attached to a strap 50 adaptable for encircling the wearer's head as shown in the embodiment of FIG. 5. A nose piece 52 joins the flanges 26 of the lenses 20 while a number of ventilation openings 54 extend though flanges 26 to allow air to freely circulate behind lenses 20.

Figure 6:
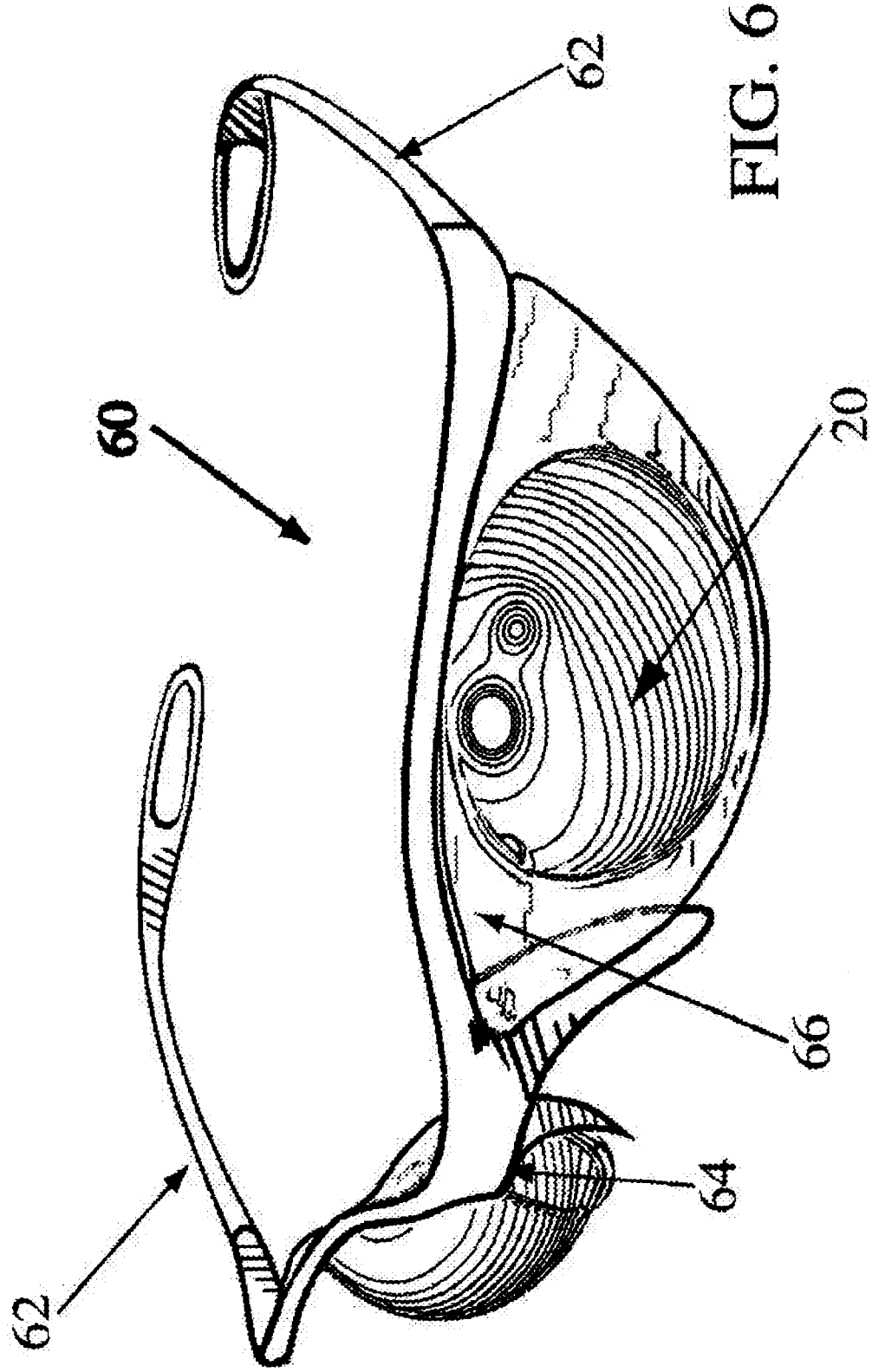
FIG. 6 is a perspective view of a pair of glasses formed in accordance with the present invention and including a pair of toric-shaped lenses formed in accordance with the present invention.

As shown in FIG. 6, a pair of lenses 20 and surrounding flanges 26 formed in accordance with the present invention are mounted in a frame assembly 60 formed of soft rubber or similar cushioning material. Frame 60 includes a pair of stems 62, which extend from the flanges 26 beyond the ears of the wearer, not shown. A nosepiece 64 supports a pair of adjacently disposed lenses 20. At least one elongated ventilation slot 66 extends between each of the toric-shaped lenses 20 and the surrounding frame 60.

Figure 7:
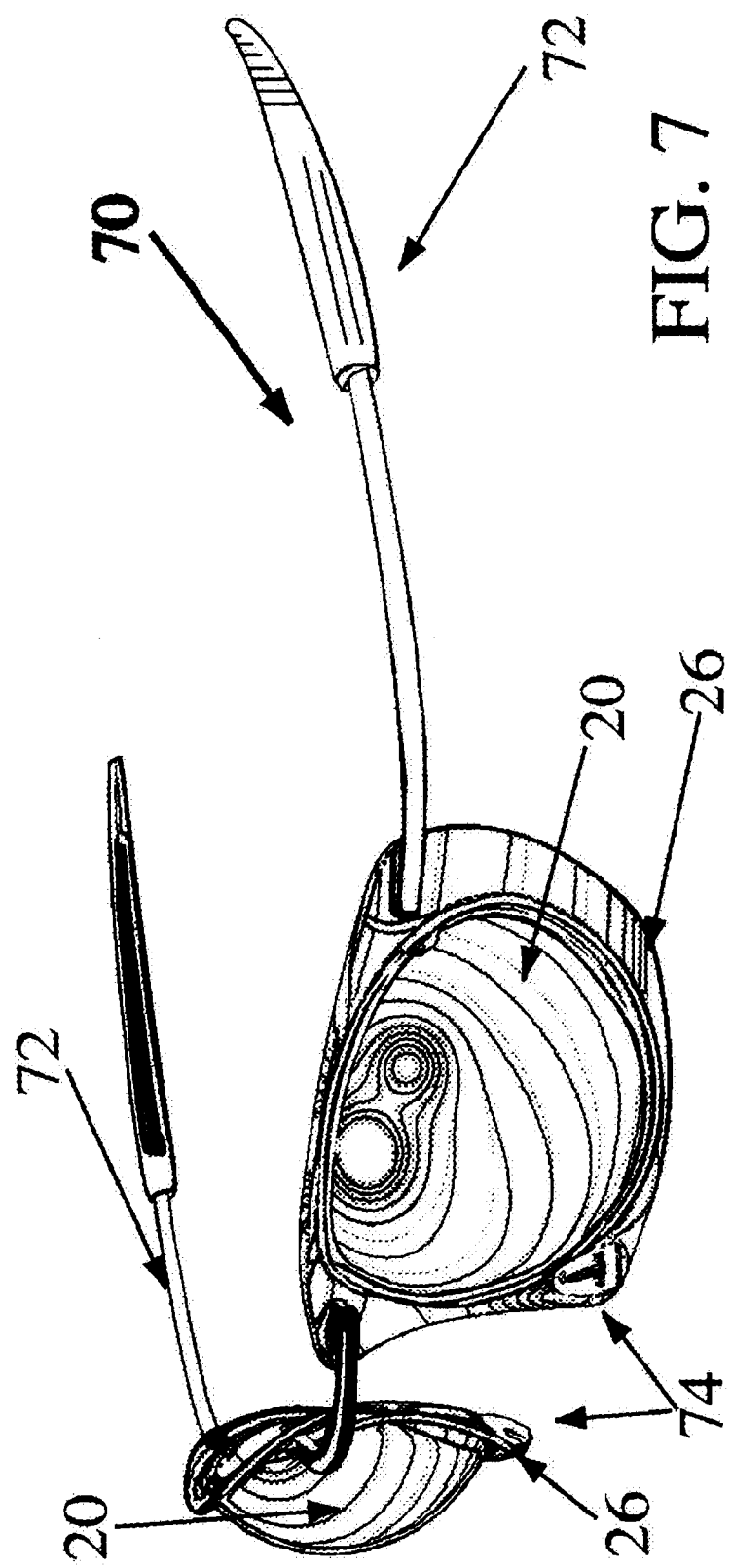
FIG. 7 is a perspective view of a further pair of glasses formed in accordance with the present invention and including a pair of toric-shaped lenses formed in accordance with the present invention.

In a further aspect of the present invention shown in FIG. 7, glasses 70 includes two lenses 20 each surrounded by a flange member 26. A pair of semi-rigid stems 72 are each connected to an outer portion of one of the flanges 26. A separate pad 74 is connected to the inner portion of each flange 26 with the pair of pads 74 serving to support the lenses 20 of glasses 70 on the bridge of the nose of the wearer, not shown. A connecting member 76 extends between flange members 26 and serves to join the lenses 20 together to form glasses 70.

Figure 8:
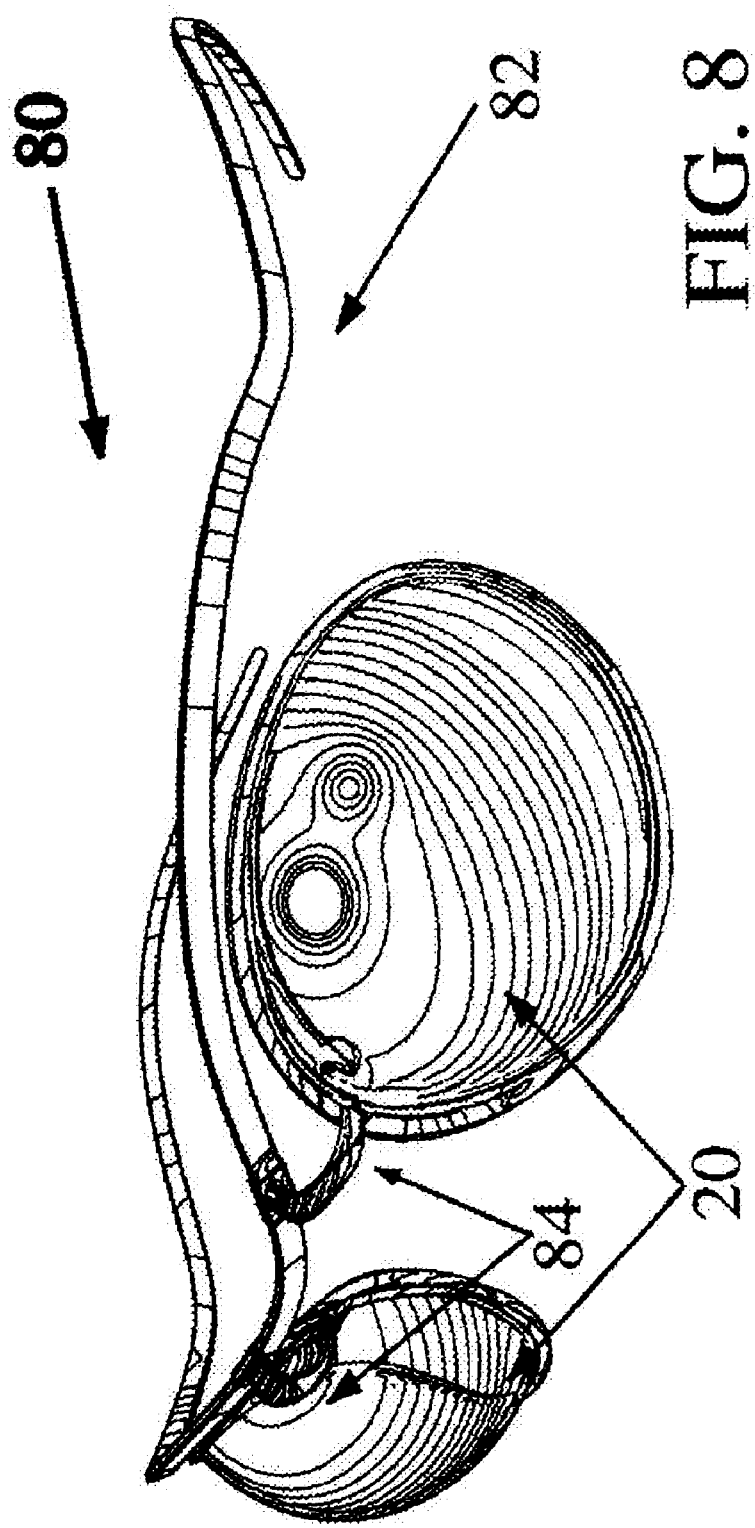
FIG. 8 is a perspective view of a further pair of glasses formed in accordance with the present invention and including a pair of toric-shaped lenses formed in accordance with the present invention.

In a yet further aspect of the present invention, the glasses 80 in FIG. 8 have eliminated the need for flanges 26. Rather, each of the pair of lenses 20 is directly connected to a frame 82 by at least one holder 84 which may comprise a wire or plastic member. It is also within the scope of the present invention for the lenses 20 to be directly connected to a pair of glass stems, a frame, paddings, and nose pieces in a manner similar to conventional lenses.

For each of the glasses or goggle assemblies formed in accordance with the present invention, the toric-shaped lenses 20 can be formed of smaller size and have an overall smaller footprint than achieved in known lenses. The lenses 20 need only surround the visible portion of the eyeball to function as effective eyewear, sunglasses or sport goggles. The overall toric lens size is selected to meet the requirements of the particular sport or fashion application. This minimalistic approach particularly benefits speed related activities, sports, and even allows for a more even sun tan. When used in sunglasses, the smaller size of the toric lens 20 offers more peripheral protection from UV rays than standard eyewear because the toric lens 20 almost entirely surrounds the exposed portion of the eyeball and can be worn much closer to the face than standard lenses.

The toric lenses 20 exhibit a more aerodynamic in design when compared to traditional lenses. More importantly, lens 20 can be individually sized to fit the eye/facial area appropriate for wearers ranging from small children to large adults. It within the scope of the present invention to create lenses 20 in various sizes, colors and materials sufficient to satisfy the vision requirements of almost any potential wearer.

The toric lens 20 can be manufactured in any color, and may include any coating or design on the front of the lenses. Because the lens 20 does not have to be completely solid, a number of ventilation openings may extend through lens 20 to assist in airflow through the lenses. This will significantly benefit a user when subjected to heat, fog or extreme weather conditions. The flange 26 surrounding lens 26 may be the same color as the lens 20 or a different color may be used to create two-toned eyewear. Glare resistant properties may be incorporated into the flange 26, while the viewing lens 20 may contain UV properties as achieved with a particular tint. Alternatively, the flanges 26 may incorporate artwork, lamination or even a personal fashion statement. The flange 26 may be formed of any material, transparent or solid.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. Distortion-free eyewear, comprising:
   a pair of toric-shaped see through lenses having a substantially constant thickness and a substantially constant radius of curvature of at least 15 mm; and
   means for retaining said pair of lenses in a fixed position relative to a wear, whereby said lenses provide a field-of-view with no discernable peripheral distortion.

2. The distortion-free eyewear according to claim 1, wherein said substantially constant radius of curvature is in the range of about 19–23 mm.

3. The distortion-free eyewear according to claim 1, wherein said means comprises a frame member supporting said pair of lenses and attached at either end to a strap assembly adaptable for surrounding a wearer's head to retain the eyewear in place.

4. The distortion-free eyewear according to claim 3, wherein said strap assembly includes a pair of elastomeric strap portions spaced from and connected to each other with end portions of one of said strap portions connected at opposite ends to said frame for securing said eyewear in place with minimal tension.

5. The distortion-free eyewear according to claim 3, wherein said strap assembly includes an elastomeric strap connected at opposite ends to said frame.

6. The distortion-free eyewear according to claim 3, wherein said frame is formed of a soft, impact resistant material and said strap assembly is formed of elastomeric, sweat absorbing material.

7. The distortion-free eyewear according to claim 1, wherein said means comprises a frame member supporting said pair of lenses and a separate stem attached to each end of said frame for supporting said eyewear.

8. The distortion-free eyewear according to claim 1, wherein each of said lenses includes at least one ventilation passageway extending completely there through, allowing air to circulate around both sides of each of the lenses.

9. Distortion-free eyewear, comprising:
   a pair of toric-shaped see through lenses having a substantially constant thickness and a substantially constant radius of curvature of at least 15 mm;
   a frame surrounding each of said lenses; and
   a support assembly for retaining said lenses and frame in place.

10. The distortion-free eyewear according to claim 9, wherein a separate flange member surrounds at least a portion of each of said toric-shaped lenses and is releasably attached to said frame.

11. The distortion-free eyewear according to claim 9, wherein a separate flange member completely surrounds each of said toric shaped lenses and is releasably attached to said frame.

12. The distortion-free eyewear according to claim 9, wherein said pair of toric lenses each has a base curve with a substantially constant radius of curvature in the range of 19–23 mm.

13. Distortion-free eyewear, comprising:
a pair of toric-shaped see through lenses having a substantially constant thickness and a base curve with a substantially constant radius of curvature of at least 15 mm;
a separate flange member surrounding and integrally attached to each of said lenses;
a frame surrounding each of said flange members, with each of said flange members releasably attached to said frame; and,
a support assembly for retaining said lenses and frame in place.

14. The distortion-free eyewear according to claim 13, wherein at least one ventilation passageway extends through said frame for allowing air to circulate around both sides of each of said lenses.

15. The distortion-free eyewear according to claim 13, wherein at least one ventilation passageway extends through each of said lenses for allowing air to circulate around both sides of each of said lenses.

16. A spectacle frame suitable for use with a series of zero-power lenses, each of the lenses having a spherical surface of radius R between 15 and 23 mm, each lens having the same value of R, said frame supporting left and right lenses in the as worn position so that the centers of the spherical surfaces are located approximately at the centroids of the left and right eyes, respectively, the frame comprising temple pieces and rim portions for engaging the left and right lenses, wherein the rim portion engaging each lens is formed in the shape of a closed curve lying on the surface of a sphere having a radius approximately equal to the radius of said spherical surface.

17. The spectacle frame of claim 16, wherein the nasal-most point and temporal-most point of the closed curve subtend an arc of greater than 90° with a vertex at the center of the spherical surface.

18. The spectacle frame of claim 16, comprising a left temple piece, a right temple piece and a nose bridge.

19. Sunglasses comprising:
left and right zero-power tinted lenses each having a spherical front surface with the same radius of curvature between about 15 mm and 23 mm; and
eyeglass frames including left and right temple pieces and a nose bridge for supporting the lenses on the face of a wearer, so that the center of the spherical front surface of each of the left and right lenses is located approximately on the centroid of rotation of the left and right eye, respectively.

20. The sunglasses of claim 19, wherein the eyeglass frame is rim less.

21. The sunglasses of claim 19, wherein:
the eyeglass frame further comprises rim portions engaging each lens; and
the lenses are tinted.

22. Goggles comprising:
left and right zero-power lenses, each of the lenses having a spherical surface of the same radius R, R being a value between 15 and 23 mm; and
a support member including left and right temples pieces and a nose bridge for supporting the lenses on the face of a wearer, so that the center of the spherical surface of each of the left and right lenses is located approximately on the centroid of rotation of the left and right eye, respectively.

23. The goggles of claim 22, wherein the radius R is greater than about 18 mm.

* * * * *